(12) United States Patent
Biris et al.

(10) Patent No.: US 9,074,187 B2
(45) Date of Patent: Jul. 7, 2015

(54) NANOSTRUCTURAL MATERIALS THAT INCREASE MINERALIZATION IN BONE CELLS AND AFFECT GENE EXPRESSION THROUGH MIRNA REGULATION AND APPLICATIONS OF SAME

(75) Inventors: Alexandru S. Biris, Little Rock, AR (US); Daniel Casciano, Little Rock, AR (US); Meena Waleed Mahmood, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 13/426,154

(22) Filed: Mar. 21, 2012

(65) Prior Publication Data

US 2012/0244224 A1  Sep. 27, 2012

Related U.S. Application Data

(60) Provisional application No. 61/454,818, filed on Mar. 21, 2011.

(51) Int. Cl.
| | |
|---|---|
| *A61K 33/00* | (2006.01) |
| *A61K 33/42* | (2006.01) |
| *A61K 9/00* | (2006.01) |
| *A61K 9/14* | (2006.01) |
| *A61K 39/395* | (2006.01) |
| *A61P 19/00* | (2006.01) |
| *A61P 19/10* | (2006.01) |
| *C12N 5/02* | (2006.01) |
| *A61K 33/24* | (2006.01) |
| *B82Y 5/00* | (2011.01) |
| *C12N 5/077* | (2010.01) |
| *A61K 33/26* | (2006.01) |
| *A61L 27/50* | (2006.01) |

(52) U.S. Cl.
CPC .............. *C12N 5/0654* (2013.01); *A61K 33/24* (2013.01); *A61K 33/26* (2013.01); *B82Y 5/00* (2013.01); *C12N 2533/10* (2013.01); *A61L 27/50* (2013.01); *A61K 9/14* (2013.01); *A61L 2400/12* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 2003/0027780 A1* | 2/2003 | Hardee et al. ................. 514/44 |
| 2008/0292714 A1* | 11/2008 | Garlich et al. ................ 424/501 |
| 2009/0035722 A1 | 2/2009 | Balasundaram et al. |
| 2010/0104652 A1* | 4/2010 | Biris et al. .................... 424/490 |
| 2010/0255447 A1* | 10/2010 | Biris et al. ................ 433/201.1 |
| 2010/0285138 A1* | 11/2010 | Biris et al. .................... 424/489 |
| 2010/0297246 A1 | 11/2010 | Weitzmann et al. |
| 2011/0190904 A1* | 8/2011 | Lechmann et al. ......... 623/23.61 |
| 2012/0141429 A1* | 6/2012 | Hass ............................ 424/93.7 |

OTHER PUBLICATIONS

Lewis, B.P. "Conserved seed pairing, often flanked by adenosines, indicates that thousands of human genes are microRNA targets" Cell, 2005, 120, 15-20.
Grimson, A. "MicroRNA targeting specificity in mammals: determinants beyond seed pairing" Mol. Cell, 2007, 27, 91-105.
Baek, D. "The impact of microRNAs on protein output" Nature, 2008, 455, 64-71.
Kaveh PourAkbar SAFFAR "Carbon Nanotubes in Bone Tissue Engineering" Department of Biomedical Engineering, Amirkabir University of Technology, Tehran, Iran; No. 26; pp. 477-498.
Target Scan database (http://www.targetscan.org/) 2 pages, Mar. 2012.
Usui, Y. "Carbon Nanotubes with High Bone-Tissue Compatibility and Bone-Formation Acceleration Effects" Small, 2008, 4, 240-246.
Oh, S. "Significantly Accelerated Osteoblast Cell Growth on Aligned TiO2 Nanotubes" J. Biomed. Mat. Res. Part A, 2005, DOI 10.1002/jbm.A, 97-103.
Wen, H.-C. "Observation of Growth of Human Fibroblasts on Silver" J. Phys.: Conf. Ser. 2007, 61, 445-449.
Zhang, L. "Nanotechnology and nanomaterials: Promises for improved tissue regeneration" Nanotoday, 2009, 4, 66-80.
Dobson, J. "Gene therapy progress and prospects: Magnetic nanoparticle-based gene delivery" Gene Therapy, 2006, 13, 283-287, doi:10.1038/sj.gt.3302720.
Zhang, Jinchao Effects of Er3+ on the proliferation, differentiation and mineralization function of a primary mouse osteoblasts in vitro. Journal of Rare Earths, vol. 29, No. 5, May 2011, pp. 507-510.
Dean, D.D. "Matrix vesicles produced by osteoblast-like cells in culture become significantly enriched in proteoglycan-degrading metalloproteinases after addition of beta-glycerophosphate and ascorbic acid" Calcif. Tissue Int. 1994, 54, 399-408.
Matsumoto, T. "Stimulation by 1,25-dihydroxyvitamin D3 of in vitro mineralization induced by osteoblast-like MC3T3-E1 cells" Bone 1991, 12, 27-32.
Mahmood, M. "Cytotoxicity and Biological Effects of Functional Nanomaterials Delivered to Various Cell Lines" J. App. Tox. 2010, 30, 74-83.
Doering, W.E. "Single-Molecule and Single-Nanoparticle Sers: Examining the Roles of Surface Active Sites and Chemical Enhancement" J. of Phys. Chem. B., 2002 106, 311-317.

(Continued)

*Primary Examiner* — Robert A Wax
*Assistant Examiner* — Danah Al-Wadi
(74) *Attorney, Agent, or Firm* — Morris, Manning & Martin, LLP; Tim Tingkang Xia, Esq.

(57) ABSTRACT

A method of inducing mineralization in a bone cell is described. The method comprises contacting a bone cell with a composition comprising nanoparticles. The nanoparticles can be single-walled carbon nanotubes, hydroxyapatite nanoparticles, $TiO_2$ nanoparticles or silver nanoparticles. The bone cell can be an osteoblast cell. A method for increasing bone mass, bone healing or bone formation is also described which comprises administering to a subject in need thereof an effective amount of a composition comprising nanoparticles. The subject can suffer from a bone disease such as osteoporosis. The subject can suffer from a bone fracture and the method can comprise contacting bone cells near the bone fracture site with the composition. The composition can further comprise a pharmaceutically acceptable carrier.

28 Claims, 10 Drawing Sheets

(56) References Cited

OTHER PUBLICATIONS

Botelho, C.M. "Human osteoblast response to silicon-substituted hydroxyapatite" J Biomed Mater Res A. 2006, 79, 723-30.

Chang, Y.L. "Calcium and phosphate supplementation promotes bone cell mineralization: Implications for hydroxyapatite (HA)-enhanced bone formation" J. Of Biomed. Mat. Res. 2000, 52, 270-278.

Liao, H. "Influence of titanium ion on mineral formation and properties of osteoid nodules in rat calvaria cultures" J. Biomed. Mater. Res. 1999, 47, 220-227.

Chen, R.J. "Noncovalent functionalization of carbon nanotubes for highly specific electronic biosensors" PNAS, 2003, 100, 4984-4989.

Shi, X. "In vitro cytotoxicity of single-walled carbon nanotube/biodegradable polymer nanocomposites" J. of Biomed. Mat. Res. 2007, 86A, 813-823.

Zhang, D. "The effects of carbon nanotubes on the proliferation and differentiation of primary osteoblasts" Nanotechnology, 2007, 18, 475102.

Magrez, A. "Cellular Toxicity of Carbon-Based Nanomaterials" Nano Lett., 2006, 6, 1121-1125.

Mahmood, M. "Synergistic enhancement of cancer therapy using a combination of carbon nanotubes and anti-tumor drug" Nanomedicine, 2009, 4, 883-893, DOI 10.2217/nnm.09.76.

Dervishi, E. "Thermally controlled synthesis of single-wall carbon nanotubes with selective diameters" J. Mater. Chem., 2009, 19, 3004-3012.

Dervishi, E. "The Influence of Fe—Co/MgO Catalyst Composition on the Growth Properties of Carbon Nanotubes" Part. Sci. And Tech., 2009, 27, 222-237.

Montjovent, M-O. "Fetal bone cells for tissue engineering" Bone, 2004, 35;1323-13331.

Kawazoe, Y. "Induction of Calcification in MC3T3-E1 Cells by Inorganic Polyphosphate" J. Dent Res, 2004, 83 (8):613-6182.

Bellows, C.G. "Mineralized bone nodules formed in vitro from enzymatically released rat calvaria cell populations" Calcit Tissue Int, 1986, 38, 143-154.

Gerstenfeld, L,C. "Expression of differentiated function by mineralizing cultures of chicken osteoblasts" Dev Biol, 1987, 122, 49-60.

Bellows, C.G. "Physiological concentrations of glucocorticoids stimulate formation of bone nodules from isolated rat calvaria cells in vitro" Endocrinology, 1987, 121,1985-1992.

Marsh, M.E. "Mineralization of bone-like extracellular matrix in the absence of functional osteoblasts" J Bone Miner Res, 1995, 10,1635-1643.

Owen, T.A. "Progressive development of the rat osteoblast phenotype in vitro: reciprocal relationships in expression of genes associated with osteoblast proliferation and differentiation during formation of the bone extracellular matrix" J. Cell Physiol, 1990, 143, 420-430.

Chen, D. "Osteoblastic cell lines derived from a transgenic mouse containing the osteocalcin promoter driving SV40 T-antigen" Mol. Cell Diff., 1995, 3, 193-212.

Gregory, C.A. "An Alizarin red-based assay of mineralization by adherent cells in culture: comparison with cetylpyridinium chloride extraction" Anal. Biochem. 2004, 329, 77-84.

Breen, E.C. "TGF beta alters growth and differentiation related gene expression in proliferating osteoblasts in vitro, preventing development of the mature bone phenotype" J. Cell Physiol. 1994, 160, 323-335.

Katayama, U.K. "Interleukin-4 enhances in vitro mineralization in human osteoblast-like cells" Biochem Biophys Res Commun, 1992, 189, 1521-1526.

Rey, C. "Structural and chemical characteristics and maturation of the calcium phosphate crystals formed during the calcification of the organic matrix synthesized by chicken osteoblasts in cell culture" J Bone Miner Res, 1995, 10, 1577—1588.

Brodersen, P. "Revisiting the principles of microRNA target recognition and mode of action" Nat. Rev. In Mol. and Cell Bio. 2009, 10, 141-148.

Chen T. "The role of microRNA in chemical carcinogenesis" J. of Env. Sci. And Health, Part C, 2010, 28, 1-36.

Li, Z. "A microRna signature for a BMP-induced osteoblast lineage commitment program" Proc. Natl. Acd. Sci., USA, 2008, 105, 13906-13911.

Chen, D. "Bone morphogenetic proteins" Growth Factors, 2004, 22, 233-241.

Beck, G.R. Jr. "Relationship between alkaline phosphatase levels, osteopontin expression, and mineralization in differentiating MC3T3-E1 osteoblasts" J. Cell Biochem. 1998, 68, 269-280.

Lee, K.S. "Runx2 is a Common Target of Transforming Growth Factor beta 1 and Bone Morphogenetic Protein 2, and Cooperation between Runx2 and Smad5 Induces Osteoblast-Specific Gene Expression in the Pluripotent Mesenchymal Precursor Cell Line C2C12" Mol. And Cell. Bio., 2000, 20, 8783-8792.

Rao, A. M. "Effect of van der Waals Interactions on the Raman Modes in Single Walled Carbon Nanotubes" Phys. Rev. Lett., 2001, 86, 3895-3898.

Dresselhaus, M. S. "Raman Spectroscopy on Isolated Single Wall Carbon Nanotubes" Carbon, 2002, 40, 2043-2061.

Strong, K. L. "Purification process for single-wall carbon nanotubes" Carbon, 2003, 41, 1477-1488.

\* cited by examiner

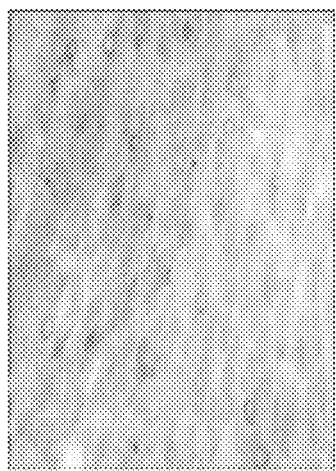 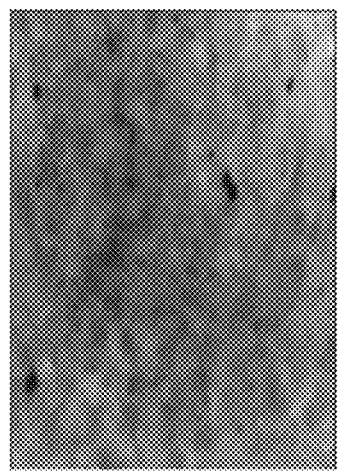 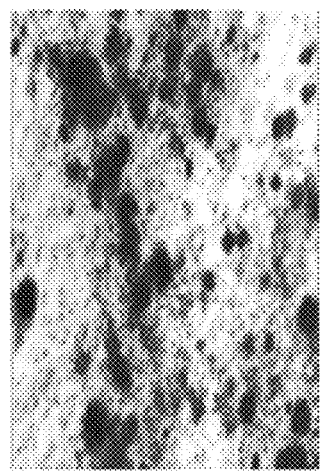
FIG. 3A   FIG. 3B   FIG. 3C
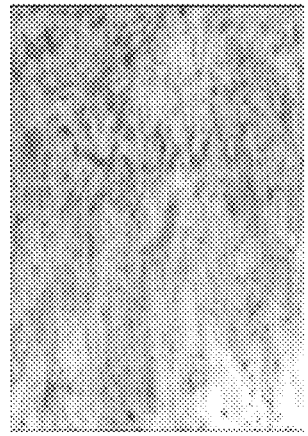 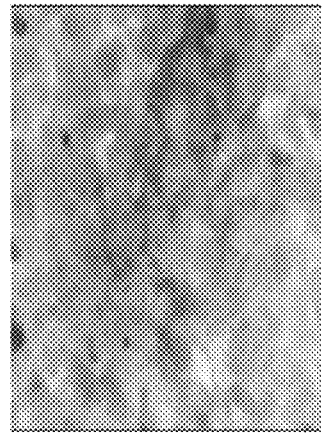
FIG. 3D   FIG. 3E

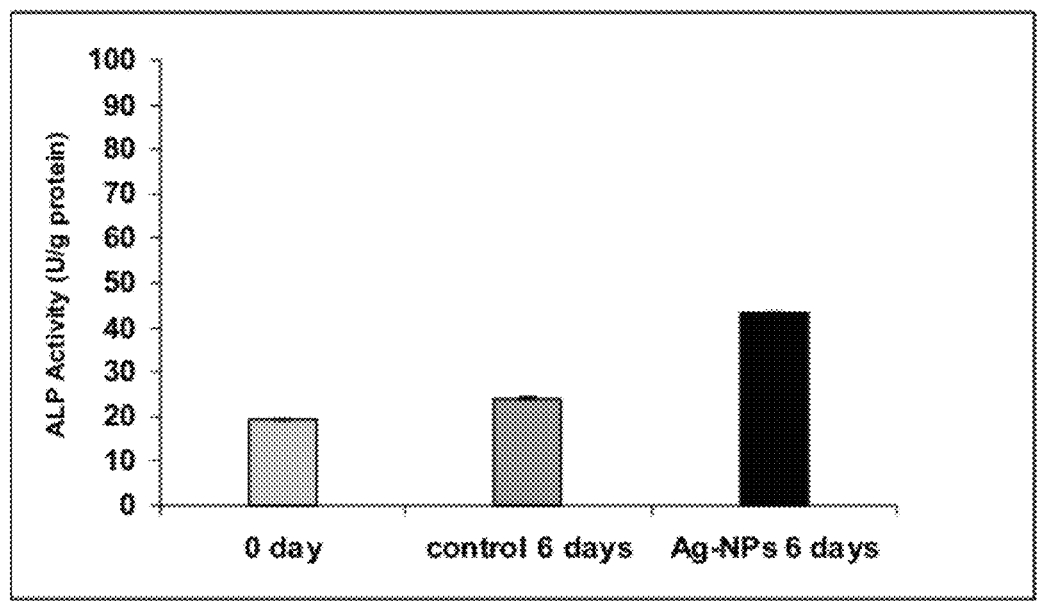
FIG. 6A
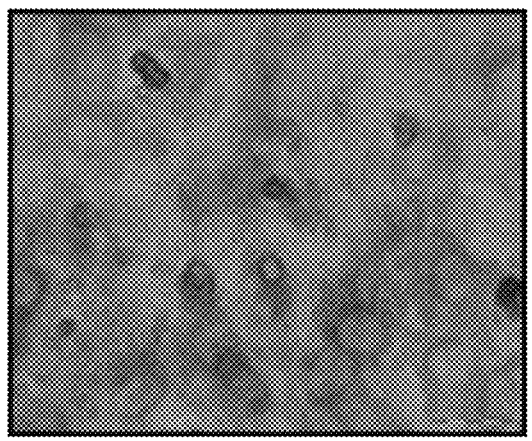 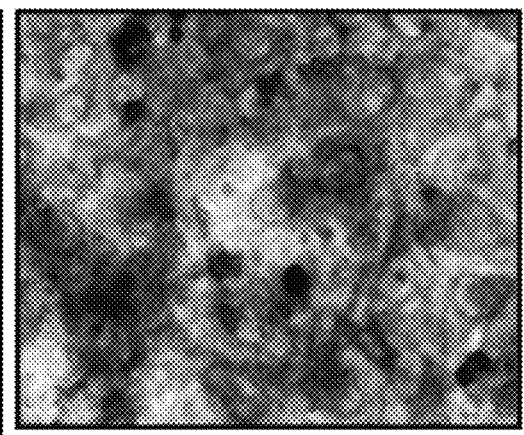
FIG. 6B     FIG. 6C

US 9,074,187 B2

NANOSTRUCTURAL MATERIALS THAT INCREASE MINERALIZATION IN BONE CELLS AND AFFECT GENE EXPRESSION THROUGH MIRNA REGULATION AND APPLICATIONS OF SAME

CROSS REFERENCE TO RELATED CASES

This application claims the benefit of Provisional U.S. Application Ser. No. 61/454,818, filed Mar. 21, 2011, which is incorporated by reference herein in its entirety.

BACKGROUND

1. Technical Field

This application relates generally to nanomaterials and, in particular, to nanomaterials that increase mineralization in bone cells and affect gene expression through miRNA regulation and to applications thereof.

Some references, which may include patents, patent application publications and various other publications may be cited and discussed in the description. The citation and discussion of such references is provided merely to clarify the description and is not an admission that any such reference is "prior art". Each reference cited in the following description is incorporated by reference herein in its entirety.

2. Background of the Technology

Bone is a living dynamic tissue and its constant rebuilding occurs through the combined action of osteoblast cells that generate bone and osteoclast cells that reabsorb it. Recently, a number of studies have focused on the growth of bone on nano-structural materials and the complex interactions between such materials and bone cells, both in vitro and in vivo [1, 2]. Because of their size and morphological properties, nanoscale materials can interact with cells and living tissues making them ideal vehicles for accelerated tissue regeneration and enhanced cellular proliferation [3, 4]. Moreover, these various shaped nanomaterials have been shown to specifically target and penetrate cells allowing delivery of genetic material [5].

SUMMARY

According to a first embodiment, a method is provided which comprises:
contacting a bone cell with a composition comprising nanoparticles;
wherein the nanoparticles induce mineralization in the bone cell.

The nanoparticles can be metal nanoparticles, metal oxide nanoparticles, carbon nanomaterials, complex nanocomposites and combinations thereof. The bone cell can be an osteoblast cell. The composition can further comprise a pharmaceutically acceptable carrier. The nanomaterial can comprise silver nanoparticles having an average diameter of 20±4 nm. The nanomaterial can comprise single-walled carbon nanotubes having a diameter of 0.8 to 1.7 nm.

According to a second embodiment, a method for increasing bone mass, bone healing or bone formation is provided which comprises administering to a subject in need thereof an effective amount of a composition comprising nanoparticles.

The nanoparticles can be metal nanoparticles, metal oxide nanoparticles, carbon nanomaterials, complex nanocomposites and combinations thereof. The subject can suffer from a bone disease such as osteoporosis. The subject can suffer from a bone fracture and the method can comprise contacting bone cells near the bone fracture site with the composition. The composition can further comprise a pharmaceutically acceptable carrier. The nanomaterial can comprise silver nanoparticles having an average diameter of 20±4 nm. The nanomaterial can comprise single-walled carbon nanotubes having a diameter of 0.8 to 1.7 nm.

BRIEF DESCRIPTION OF THE DRAWINGS

The skilled artisan will understand that the drawings, described below, are for illustration purposes only. The drawings are not intended to limit the scope of the present teachings in any way.

FIG. 2 is a representative photomicrograph showing the characteristic features of bone cells stained with methyl green wherein FIG. 2A shows a control which is unexposed to nanomaterials, FIG. 2B shows bone cells incubated with AgNPs, FIG. 2C shows bone cells incubated with SWCNTs, FIG. 2D shows bone cells incubated with HAP nanoparticles, and FIG. 2E shows bone cells incubated with $TiO_2$.

FIG. 3 shows the mineralized nodule formation of osteoblasts in the presence of nanomaterials stained by Alizarin Red stain wherein FIG. 3A shows cells without nanomaterials, FIG. 3B shows cells incubated with AgNPs, FIG. 3C shows cells incubated with HAP nanoparticles, FIG. 3D shows cells incubated with $TiO_2$, nanoparticles, FIG. 3E shows cells incubated with SWCNTs.

FIG. 6 shows the increased level of ALP activity for the cells exposed to AgNPs for 24 hours and further incubated in fresh medium for 6 days wherein FIG. 6A is a graph showing the effect of AgNPs on the ALP activity of MC3T3-E1 cells, FIGS. 6B and 6C are microscopic images showing a control (FIG. 6B) and the enhanced level of ALP after 6 days post Ag-NP exposure (FIG. 6C) wherein the cells were stained by ALP double staining and the level of the ALP enzyme was evaluated.

DETAILED DESCRIPTION

Figure 1:
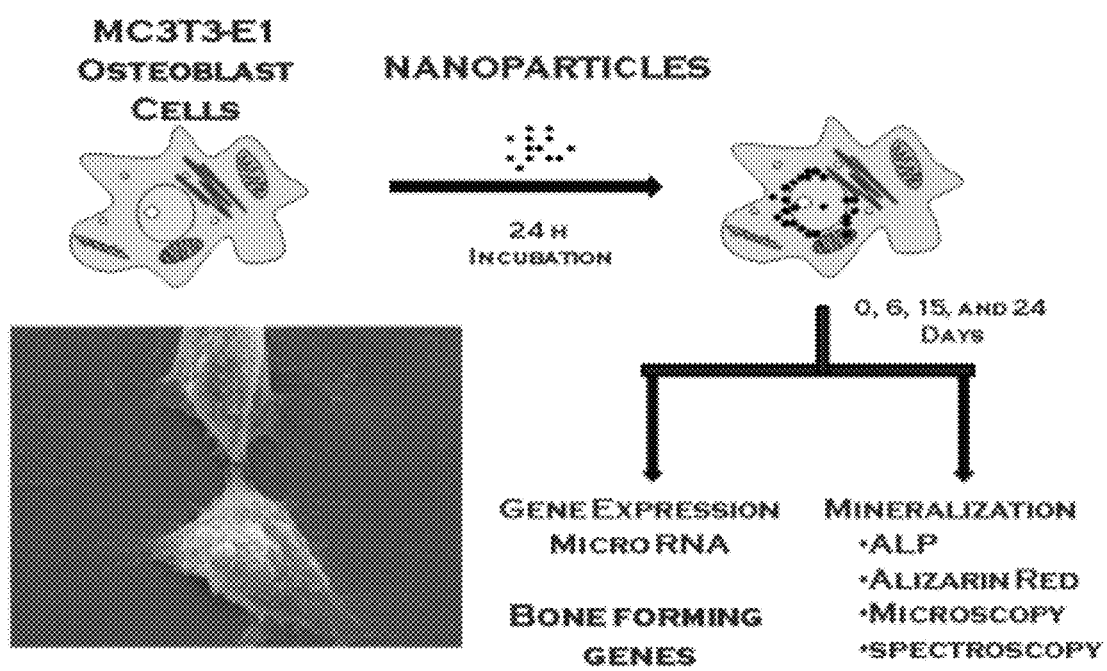
FIG. 1 is a diagram showing an experimental design wherein MC3T3-E1 cells are incubated with nanomaterials and the effects of the nanoparticles on miRNA expression and mineralization were assessed.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

As used herein, a nanomaterial or a nanostructural material is a material having at least one dimension of less than 100 nm.

As used herein, a nanoparticle is a particle having at least one dimension of less than 100 nm.

As used herein, a bone cell is any cell that is found in bone. Bone cells include osteoblasts, osteocytes, osteoclasts, osteoprogenitors and bone lining cells. Osteoblasts are commonly called bone-forming cells. They secrete osteoid, which forms the bone matrix. They also begin mineralization. Osteocytes are mature osteoblasts which no longer secrete matrix, yet are surrounded by it. Osteocytes maintain metabolism, and participate in nutrient/waste exchange via blood. Osteoclasts function in resorption and degradation of existing bone, the opposite of osteoblasts. Osteoprogenitors are immature cells which differentiate to make osteoblasts. Bone lining cells are quiescent osteoblasts covering the bone.

AgNPs have been widely used as a biomaterial in a number of biomedical applications ranging from anti-microbial coatings to surface enhanced Raman Spectroscopy sensing [10, 11]. Hydroxyapatite (HAP) is one of the most commonly used materials in bone graft because of its demonstrated ability to enhance mineral formation and promote bone calcification during in vitro and in vivo experiments [12, 13]. Although it has a high potential in bone regeneration, the HAP bio-reactivity when in a nanostructural form, is still not fully understood. Titanium Dioxide ($TiO_2$) is one of the most corrosion-resistant materials that has been used intensively in orthopedics, dentistry and a number of other applications [14]. Also it was previously shown that $TiO_2$ nano-morphologically modified coatings can be used to reduce the adverse inflammatory effects of titanium implants and promote more advanced tissue healing following surgical procedures [15]. Single Walled Carbon Nanotubes (SWCNTs) are superb one-dimensional nanostructures and their use in bio-medical applications range from highly accurate and sensitive biosensors [16], scaffolds for bone regeneration [17], and other bio-medical applications [18, 19]. Moreover, it has previously been shown that carbon nanotubes can synergistically enhance the activity of various drugs [20]. SWCNTs having a diameter ranging between 0.8 and 1.7 nm and an average length of several microns were prepared according to the methods described below [21, 22].

As described below, it has been found that nanomaterials can greatly enhance the level of the extracellular matrix formation and mineral deposition by MC3T3-E1 cells and the response was a function of the type of nanomaterials used. The most significant enhancement of cellular mineralization was observed using Ag-NPs, followed by the HAP, $TiO_2$ and SWCNTs. Interestingly, all the nanomaterials used in this study induced a higher mineralization in the MC3T3-E1 cells when compared to the control (i.e., untreated cells). Although the mechanism that govern the interactions between the nanomaterials and cells are not fully understood and while not wishing to be bound by theory, it is thought that the nanomaterials may increase osteoblast cell cAMP production and intracellular calcium levels, affect DNA synthesis, alter collagen protein production and/or to be closely related to regulation of alkaline phosphatase activity [23, 24].

Since nanomaterials have been observed to penetrate various sub-cellular compartments, including the nucleus, they may have the potential to alter normal biological processes. Given that the nanoparticles increased mineralization in these particular cells, they are expected to have an affect on the activity of alkaline phosphatase found on the bone cell membrane and which is considered an essential marker for bone cell proliferation and differentiation [7]. Alizarin Red, a dye that is used to stain inorganic calcium deposition [25, 26], mineralized vs. the unmineralized nodules [27], mineral deposition [28, 29], mineralized matrix [30]and mineralized bone nodule formation has been used extensively to study and quantify bone differentiation in model cell systems. In addition to Alizarin Red staining, electron diffraction spectroscopy (EDS), scanning electron microscopy (SEM), X-ray diffraction (XRD) and Raman spectroscopy [31, 32, 33, 34] have been used to examine and quantify mineralization of inorganic calcium formed by the bone cells.

In addition to the observed phenotypic responses to the nanoparticles, the underlying molecular processes responsible for these observations has been investigated. The genes associated with MC3T3 mineralization were identified by evaluating microRNA regulation at various times subsequent to exposure of the cells to control media and control media supplemented with AgNPs (see Materials and Methods section below). MicroRNAs (miRNAs) comprise a family of 21-25 nucleotide non-coding small RNAs that regulate gene expression at the post-transcriptional level and participate in the regulation of almost every cellular process that has been investigated [35]. Currently, only a small number of miRNA target genes have been identified via direct experimentation. Instead, bioinformatic approaches, such as TargetScan, are used to determine the general principles governing miRNA target recognition and mechanism of action [36]. Recently, a study by Li et al. detected miRNAs related to osteogenic differentiation induced by bone morphogenetic protein 2 (BMP2)-exposed premyogenic C2C12 cultured cells [37]. They found that the miRNA predicted targets included the transcription factors Runx2, Msx2, Dlx3, SMAD1 and SMAD5, as well as members of the Wnt/β-catenin pathway and BMPs and their receptors, and other signaling pathways that have been reported to promote osteogenesis. They concluded that BMP2 controls bone cell determination in this model in vitro cell system via a variety of different mechanisms. BMPs are multifunctional growth factors that play critical roles in embryonic development and cellular functions in postnatal and adult animals including acting as potent stimulators of bone formation [38].

A method is provided which comprises:
contacting a bone cell with a composition comprising a nanomaterial selected from the group consisting of: single-walled carbon nanotubes; hydroxyapatite nanoparticles; $TiO_2$ nanoparticles; and silver nanoparticles;
wherein the nanoparticles induce mineralization in the bone cell.

The bone cell can be an osteoblast cell. The composition can further comprise a pharmaceutically acceptable carrier. The nanomaterial can comprise silver nanoparticles having an average diameter of 20±4 nm. The nanomaterial can comprise single-walled carbon nanotubes having a diameter of 0.8 to 1.7 nm.

A method for increasing bone mass, bone healing or bone formation is also provided which comprises administering to a subject in need thereof an effective amount of a composition comprising a nanomaterial selected from the group consisting of: single-walled carbon nanotubes; hydroxyapatite nanoparticles; $TiO_2$ nanoparticles; and silver nanoparticles.

The subject can suffer from a bone disease such as osteoporosis. The subject can suffer from a bone fracture and the method can comprise contacting bone cells near the bone fracture site with the composition. The composition can further comprise a pharmaceutically acceptable carrier. The nanomaterial can comprise silver nanoparticles having an average diameter of 20±4 nm. The nanomaterial can comprise single-walled carbon nanotubes having a diameter of 0.8 to 1.7 nm.

Several nanomaterials were found to induce enhanced mineralization (increased numbers and larger areas of mineral nests) in MC3T3-E1 bone cells, with the highest response being induced by silver nanoparticles (AgNPs). It has also been demonstrated that AgNPs altered microRNA expression resulting in specific gene expression associated with bone formation. Essential transcriptional factors and bone morphogenetic proteins have been identified that play an important role in activation of the process of mineralization in bone cells exposed to AgNPs.

Other nanoparticles may also be used. Exemplary and non-limiting examples of nanoparticles which may be used include metal nanoparticles (e.g., gold, silver, Pt, Pd, Ru, Al, Fe); metal oxide nanoparticles (e.g., $Al_2O_3$, $SiO_2$, ZrO, $TiO_2$, hydroxyapatite); carbon nanomaterials (e.g., carbon nanotubes such as single-walled, double-walled and multi-walled carbon nanotubes, graphene, and nanofibers); complex nanocomposites; and mixtures of any of the above-described types of nanoparticles. According to some embodiments, the nanoparticles can be coated with a layer of polymer. According to some embodiments, the nanoparticles can be attached to one or more targeting molecules (e.g., antibodies, folates, growth factors, etc.). The nanoparticles can be of any shape. According to some embodiments, the nanoparticles can be spherical, nanorods, nanotubes, or flat sheets.

EXPERIMENTAL

The practice of this invention can be further understood by reference to the following examples, which are provided by way of illustration only are not intended to be limiting.

Osteoblast cells (MC3T3-E1 cell line, derived from newborn mice calvaria) were incubated with various nanomaterials in order to study the effects of such structures on the biological activity of the cells, with a focus on mineralization rates. This type of cell was shown to be a model system for studying complex biological processes related to mineralization and bone formation of the osteoid matrix [6]. Additionally, they were found to readily interact with nanostructural materials and the observed effects could be translated to in vivo conditions with potentially positive benefits for the treatment of a number of bone related conditions, such as osteoporosis, or resorption of tissues. Here we report the in vitro effects of various types of nanomaterials (single walled carbon nanotubes -SWCNTs, hydroxyapatite nanoparticles -HAP, titanium dioxide nanoparticles —$TiO_2$, and silver nanoparticles AgNPs) on cell calcification and mineralization by MC3T3-E1 cells [7, 8], which display time-dependent and sequential expression of osteoblast characteristics similar to that found in in vivo bone tissue. The aforementioned nanomaterials were chosen due to their relevance to specific areas of nanoscience and their significant potential in bio-medical applications. Silver nanoparticles (AgNPs) with an average diameter of 20±4 nm were used in this study [9].

FIG. 1 shows the experimental design used in this study. As shown in FIG. 1, MC3T3-E1 cells were incubated with nanomaterials for 24 hours, after which the nanomaterials were removed. This point was considered as Day 0. The cells were incubated with either control medium or with medium plus nanoparticles for 24 hours. After removal of the nanoparticles, the cultures were further incubated with fresh medium. In particular, the cells were further incubated with fresh medium and Osteo I and/or Osteo II media for up to 24 days and the effects of the nanoparticles on miRNA expression and mineralization were assessed on days 6, 15, and 24. At confluence (Day 6), all of the cultures were supplemented with Osteo I medium for 6 days and then supplemented with Osteo II medium and further cultured to day 24. In the cultures treated with AgNPs, in addition to mineralization, miRNAs expression was also analyzed at 6, 15, and 24 days after the treatment with these nanoparticles.

Figure 2:
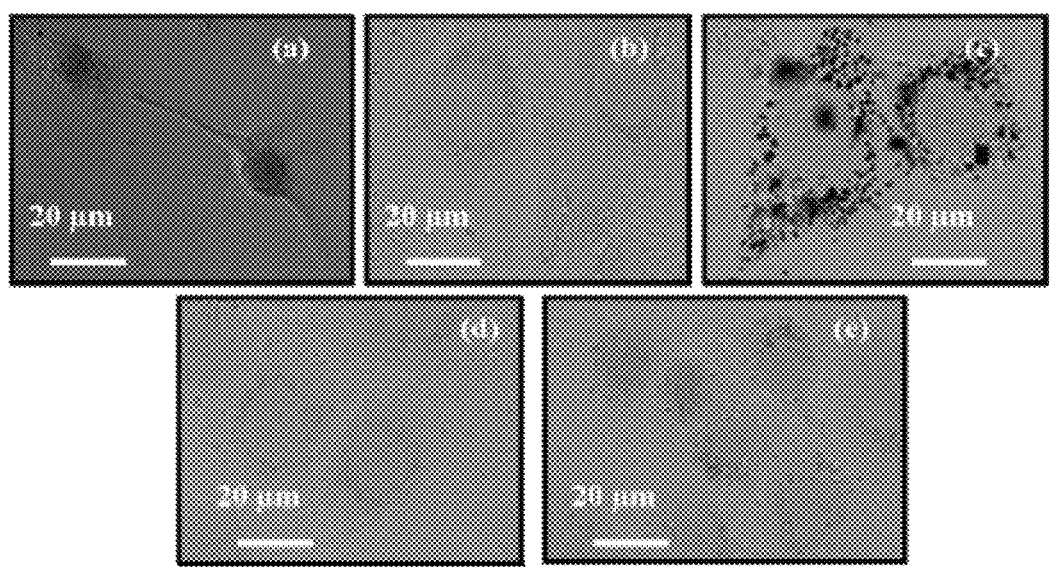

During the 24 hour incubation process, the nanoparticles appear to have penetrated cells suggesting their possible location in the cytoplasm and nucleus. FIG. 2 shows the optical images of the MC3T3-E1 cells before and after incubation with the four types of nanomaterials used in this study. FIG. 2 is a representative photomicrograph showing the characteristic features of the bone cells stained with methyl green wherein FIG. 2A shows a control which is unexposed to nanomaterials, FIG. 2B shows bone cells incubated with AgNPs, FIG. 2C shows bone cells incubated with SWCNTs, FIG. 2D shows bone cells incubated with HAP and FIG. 2E shows bone cells incubated with $TiO_2$. It is clearly seen from FIG. 2 that most of the nanoparticles coalesce around the nucleus while some appeared to penetrate and accumulate inside the nucleus. As a result, they are expected to strongly interact with the various sub-cellular environments and possibly produce significant genetic and functional modifications.

Effect of Nanomaterials on Cell Mineralization in Vitro

Figure 3F:
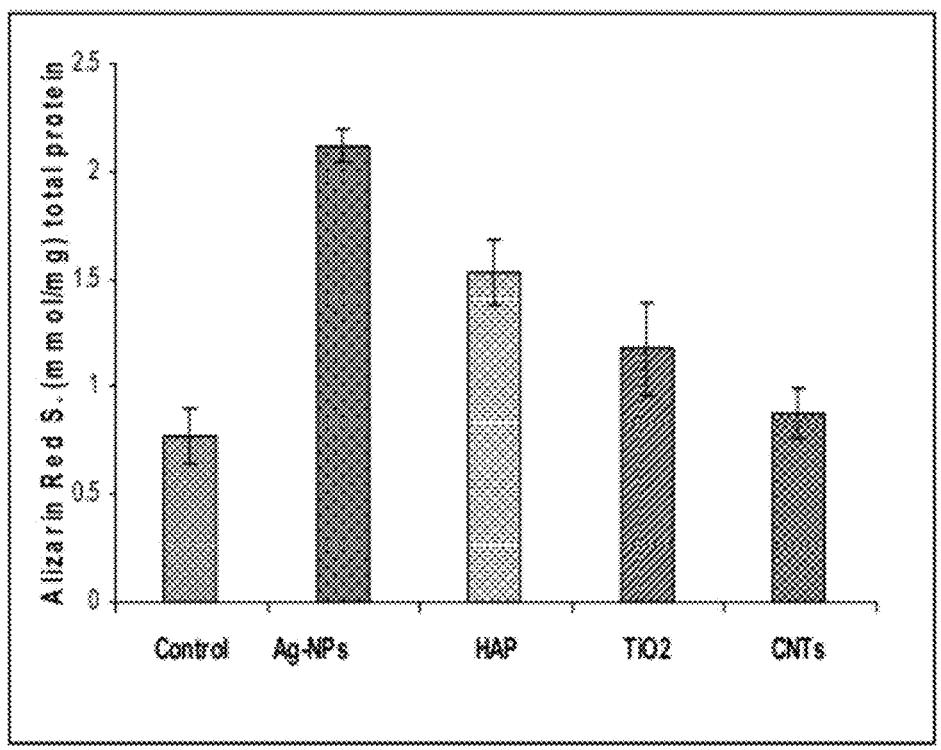
FIG. 3F shows the effect of nanomaterials type on the concentration of Alizarin Red S. stain when osteoblastic bone cells were incubated in the presence of (20 µg/ml) of AgNPs, HAP, $TiO_2$ and SWCNTs compared with the control samples.
Figure 3G:
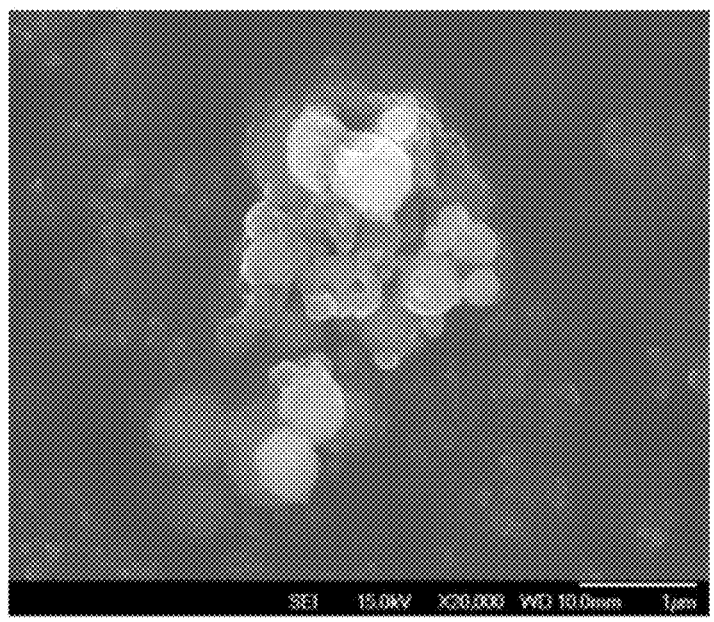
FIG. 3G is an SEM analysis of the mineralization nests.
Figure 3H:
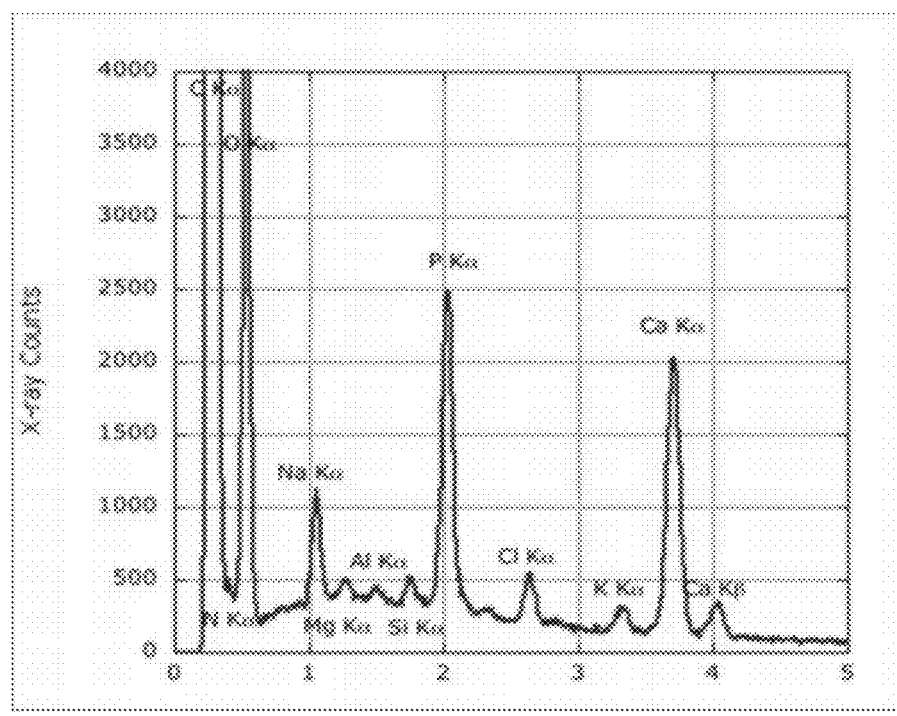
FIG. 3H shows elemental analysis of the mineral nests performed by EDS and indicating the specific elements presents in the mineral tissue.

The formation of mineralized bone nodules is considered a marker for the final stages of osteoblast differentiation and can be analyzed and quantified by staining fixed cell populations with Alizarin Red S (ARS). To demonstrate the value of alizarin red staining in the observation of mineralized nodule formation, the conditions up to 24 days of culture have been imaged. FIG. 3 shows the mineralized nodule formation of osteoblasts in the presence of nanomaterials stained by Alizarin Red stain. All samples were incubated with Osteo I and II differentiation media (cf. M&M). FIG. 3A shows cells without nanomaterials. FIG. 3B shows cells incubated with AgNPs. FIG. 3C shows cells incubated with HAP. FIG. 3D shows cells incubated with $TiO_2$. FIG. 3E shows cells incubated with SWCNTs. FIG. 3F shows the effect of nanomaterials type on the concentration of Alizarin Red S. stain when osteoblastic bone cells were incubated in the presence of (20 μg/ml) of AgNPs, HAP, $TiO_2$ and SWCNTs compared with the control samples. FIG. 3G is an SEM analysis of the mineralization nests. FIG. 3H shows elemental analysis of the mineral nests performed by EDS and indicating the specific elements presents in the mineral tissue. The experiments were assessed on day 24. Alizarin Red concentrations were determined by comparing the samples $OD_{405}$ with a standard sample of 2 mM of ARS diluted with 1× ARS dilution buffer and expressed as the concentration of the eluted Alizarin Red S. normalized by the standard protein.

Elution and analysis of the ARS levels bound to the mineralized nodules (FIGS. 3A-3E) confirmed an enhanced matrix formation in the osteoblast cell cultures that were exposed to the four types of nanomaterials. The results showed that there was negligible staining for the control cells grown in Osteo I & II media (unexposed to any nanoparticles) with only few areas of weak Alizarin Red staining (FIG. 3A). The effect of enhanced mineralization varied with the type of nanomaterials, with the AgNPs having the most significant effect (FIG. 3F). FIGS. 3G and 3H show the scanning electron microscopy (SEM) and elemental analysis (EDS) of the mineralization nests, indicating the presence of Ca, P, O typical to mineralized structures.

Figure 4:
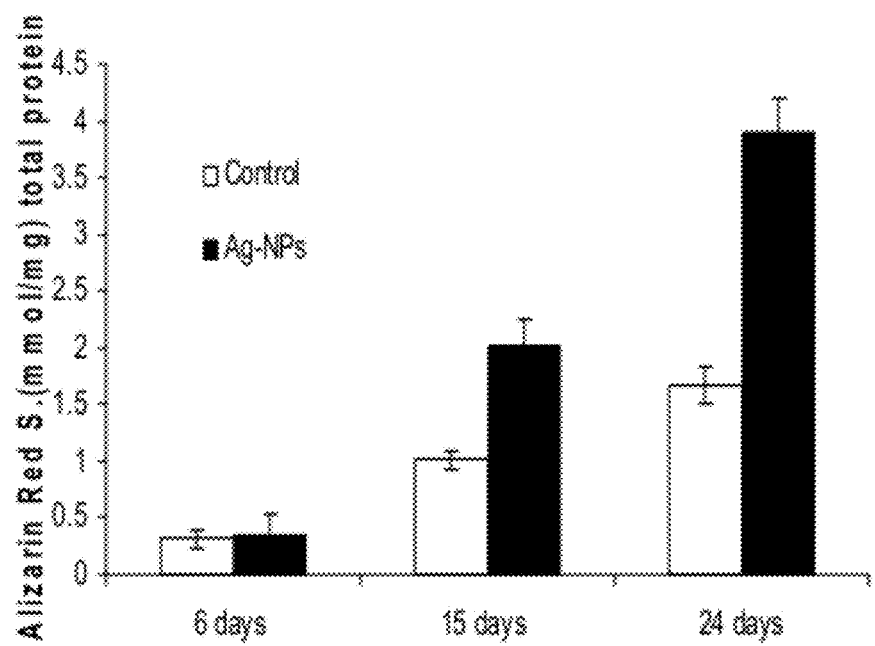
FIG. 4 is a bar chart showing the effect of silver nanoparticles on the concentration of Alizarin Red stain as a function of time wherein $10^5$ cells were plated per 35 mm well with silver nanoparticles (20 µg/ml) and without silver nanoparticles (control) and incubated for 6, 15, and 24 days and wherein the bars represent the concentration of the eluted Alizarin Red S. stain which is normalized with the standard dye.
Figure 5A:
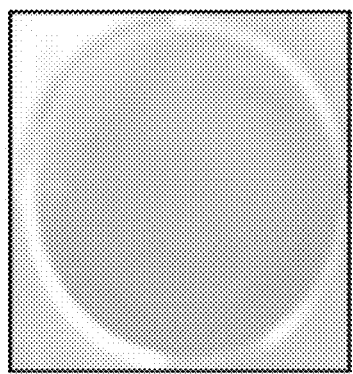
FIGS. 5A-5F show the actual stained Petri dishes clearly indicating that the cells exposed to AgNPs induced higher mineralization (darker color) throughout the 24 days (FIGS. 5D-5F) as compared to the controls (FIGS. 5A-5C) wherein the actual stained petri dishes with Alizarin Red for control and the cell cultured with AgNPs for 6 days (FIGS. 5A and 5D), 15 days (FIGS. 5B and 5E), and 24 days (FIGS. 5C and 5F).
Figure 5B:
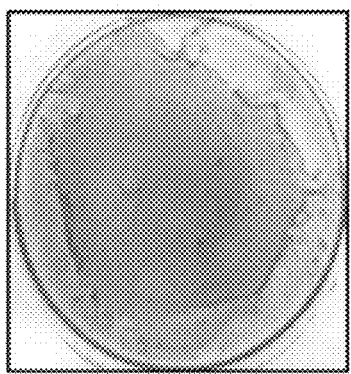
Figure 5C:
Figure 5D:
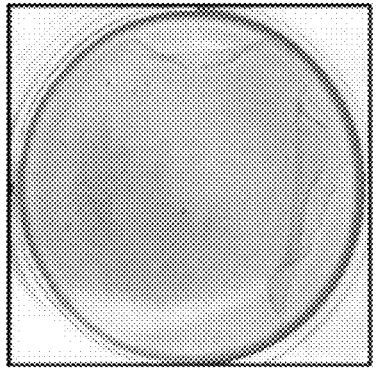
Figure 5E:
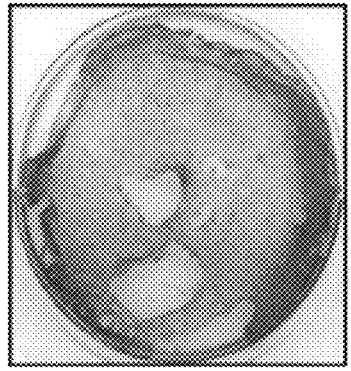
Figure 5F:
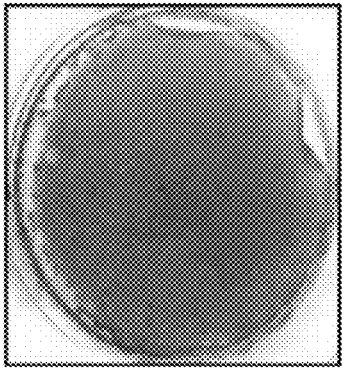

Since the AgNPs induced the highest level of mineralization (increase in both area and intensity of mineralized nodules) when introduced into cell cultures, AgNPs were further used to investigate the kinetics of mineral formation at several time periods (6, 15, and 24 days). FIG. 4 shows the effect of silver nanoparticles on the concentration of Alizarin Red stain as a function of time, $10^5$ cells were plated per 35 mm well with and without silver nanoparticles (20 μg/ml) and incubated for 6, 15, and 24 days. The results were derived from 3 experiments, with 6 cultures for each variable in each experiment. Bars represent the concentration of the eluted Alizarin Red S. stain which is normalized with the standard dye. FIGS. 5A-5F show the actual stained Petri dishes clearly indicating that the cells exposed to AgNPs induced higher mineralization (darker color) throughout the 24 days (FIGS. 5D-5F) as compared to the controls (FIGS. 5A-5C) wherein the actual stained petri dishes with Alizarin Red for control and the cell cultured with AgNPs for 6 days (FIGS. 5A and 5D), 15 days (FIGS. 5B and 5E), and 24 days (FIGS. 5C and 5F).

As can be seen from FIGS. 4 and 5, a significant increase in the level of Alizarin Red stain can be observed for the cells exposed to AgNPs when compared to the control and the trend was found to increase as the time progressed from 6 to 15 and 24 days of incubation.

Induction of Alkaline Phosphatase (ALP) Activity by AgNPs

Figure 6D:
FIGS. 6D and 6E are actual images of the ALP stained Petri dishes for the control (FIG. 6D) and the cells exposed to AgNPs and cultured for 6 days (FIG. 6E).
Figure 6E:
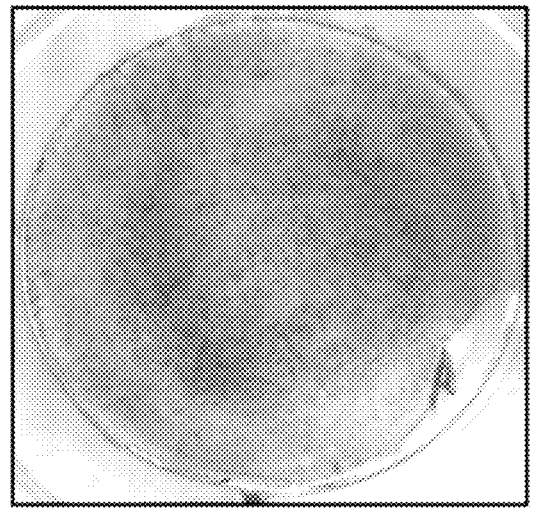

ALP is an enzyme commonly used as a marker for the calcification level during the bone maturation process [39]. The effect of the AgNPs on ALP activity and level was measured at various points in time. The level of ALP was found to increase significantly when the cells were exposed to AgNPs, as compared to the control samples, confirming the increased level of mineralization presented in FIGS. 3, 4 and 5. FIG. 6 shows the increased level of ALP activity for the cells exposed to AgNPs for 24 hours and further incubated in fresh medium for 6 days. In particular, FIG. 6A is a graph showing the effect of AgNPs on the ALP activity of MC3T3-E1 cells. FIGS. 6B and 6C are microscopic images showing a control (FIG. 6B) and the enhanced level of ALP after 6 days post Ag-NP exposure (FIG. 6C). The cells were stained by ALP double staining and the level of the ALP enzyme was evaluated. FIGS. 6D and 6E are actual images of the ALP stained Petri dishes for the control (FIG. 6D) and the cells exposed to AgNPs and cultured for 6 days (FIG. 6E).

While not wishing to be bound by theory, it has been hypothesized that certain marker morphogenetic proteins and/or important transcriptional factors could be involved in the effects observed in cells exposed to AgNPs. In order to identify the target-genes involved in activation of mineralization in response to AgNPs, miRNA microarray analysis was performed. This assay was recently used for identification of gene-targets that are positive regulators of bone formation [37]. In our set of experiments, miRNA assessment allowed us to determine structural and regulatory genes required for bone formation that were significantly affected in control cultures of MC3T3-E1 cells, as well as cultures that were exposed to silver nanoparticles. We chose to detect miRNA expression profiles on the same days that the phenotypic response to AgNPs was determined (FIG. 4).

Table 1 and 2 shows selected up-regulated miRNAs and predicted gene-targets, associated with particular miRNAs, in control cells and cells exposed to AgNPs at three time points. Although several bone morphogenetic proteins (BMPs) were affected in the control cells due to the presence of osteogenesis differentiation media, there was a delay of several days in miRNA regulation of expression for a number of BMPs compared with the AgNPs exposed cultures (Tables 1, 2). Thus, no BMP gene-targets were detected on day 6 of culture in the controls, while a large number of these multifunctional bone forming growth factors were observed on day 6 in the AgNPs exposed cultures. Additionally, the exposure of cells to AgNPs not only resulted in the miRNA regulation of similar BMPs that were found in the control cultures, but also included several gene-target BMPs not found in the controls; for example BMP3, BMP6, BMP7, and BMP8B. BMP2 is a critical protein required to induce osteoblast differentiation and the AgNPs were found to induce expression of miRNAs associated with the gene that is responsible for the production of this protein on day 6 of the experiment.

The data presented in Tables 1 & 2 support the hypothesis that significant changes in microRNAs that are related to the regulation of BMPs in cells exposed to silver nanoparticles play an important role in the process of mineralization in these cells. In particular, it has been found that miRNA regulation of essential transcriptional factors involved in osteoblast formation exhibited a similar trend that was documented for BMPs. The up-regulation of several miRNAs related to transcription factors was delayed in control (unexposed) cells compared to AgNPs-exposed cells (Tables 1 & 2). Regulation of miRNAs that can affect SMAD5 transcriptional factor appeared on day 6 in AgNPs-exposed cells but not in control cells. The number of transcriptional factors associated with bone formation such as Runx2, DLX3, MSX2 were affected by correspondent miRNAs only in cells exposed to AgNPs. Runx2 is a common target of transforming growth factor β1 and bone morphogenetic protein 2, and cooperation between Runx2 and Smad5 induces osteoblast-specific gene expression in the pluripotent mesenchymal precursor cell line C2C12 [40]. Lee et al. have also showed that Runx2 was a major target of BMP2 in pluripotent mesenchymal cells and that osteoblast specific gene expression was also dependent on the transcription factor Smad5, an upstream regulator of Runx2 [40]. The data in Tables 1 & 2 indicate that AgNPs are not only responsible for the miRNA regulation of expression of Smad1/5 but also of Runx2. Both Runx2 and Smad1/5 are transcription factors essential for osteogenesis and activate bone-specific genes in a synergistic way. The difference in the regulation of BMPs and their transcription factors is most likely responsible for the differential Alizarin stain intensity observed in FIG. 3 and FIG. 4.

Further investigation of the "cross-talk" between transcriptional factors and BMPs in bone cells can be used to understand the mechanism(s) by which nanoparticles, especially AgNPs, enhance bone formation. The data indicate that engineered nanomaterials can play a significant role in bone mineralization at the genomic level. These findings support the development of nanoparticles-based treatments for a number of medical conditions that involve bone resorption or loss.

TABLE 1

Regulatory Genes (Transcriptional Factors) and Selected Structural Genes Regulated by Over-Expression of MiRNAs in Control Cells Grown in the Presence of Osteogenesis I and II Growth Media

| Day of exposure | miRNA related to putative structural genes | Putative structural genes (gene-targets of miRNAs) | miRNA related to putative transcription factors | Putative transcription factors (gene-targets of miRNAs) |
|---|---|---|---|---|
| 6 | None | None | None | None |
| 15 | mir-874 | BMP1 | mir-133; | Dlx3 |
|  | mir-142-5p; | BMP2 | mir-142-5p | Smad1 |
|  | mir-17 | BMPR1B | mir-300; let-7d | Smad5 |
|  | mir-101a | BMPR2 | mir-17 |  |
|  | mir-17 | CRIM1 |  |  |
|  | mir-17 |  |  |  |
| 24 | mir-345-5p | BMP2 | mir-497 | Smad5 |
|  | mir-497 | BMPR1A |  |  |
|  | mir-361 | BMPR2 |  |  |
|  | mir-497 | BMP8A |  |  |

BMP1, BMP2, BMP8A - Bone morphogenetic protein 1, 2, 8A, respectively;
BMPR1A, BMPR1B - Bone morphogenetic protein receptor, type 1A, type 1B, respectively;
BMPR2 - Bone morphogenetic protein receptor, type 2;
CRIM1 - Cysteine rich transmembrane BMP regulator 1;
Dlx3 - Distal-less 3 homeobox gene;
Smad1 and Smad5 - Mothers against decapentaplegic transcription factor.

TABLE 2

Regulatory Genes (Transcriptional Factors) and Selected Structural Genes Regulated by Over-Expression of MiRNAs in Cells Exposed To Osteogenesis I and II Growth Media in Presence of Ag-NPs

| Day of exposure | miRNA related to putative structural genes | Putative structural genes (gene-targets of miRNAs) | miRNA related to putative transcription factors | Putative transcription factors (gene-targets of miRNAs) |
|---|---|---|---|---|
| 6 | mir-374 | BMP2 | mir-130a; mir-130b | SMAD5 |
|  | mir-374 | BMP3 |  |  |
|  | mir-29b | BMPR1A |  |  |
|  | mir-721 | BMPR1B |  |  |
|  | mir-721 | BMPR2 |  |  |
|  | mir-295; mir-374 | CRIM1 |  |  |
| 15 | mir-124 | BMP6 | mir-325; mir-30b, mir-217; | Runx2 |
|  | mir-325 | BMP7 | mir-466d-3p; | Msx2 |
|  | mir-16 | BMP8A | mir-23b | Dlx3 |
|  | mir-331-3p; mir-763 | BMP8B | mir-381 | Smad1 |
|  | mir-503; mir-29b; | BMPR1A | mir-19a; mir-29c | Smad5 |
|  | mir-29c; mir-16; | BMPR1B | mir-182; mir-291-5p; mir-30b |  |
|  | mir-130a; mir-130b; mir-721; | BMPR2 | mir-130a; mir-130b; mir-721; |  |
|  | mir-381 | BMPER | mir-224; mir-19a; mir-106b; |  |
|  | mir-466d-3p; mir-101b; mir-124 | CRIM1 | mir-93; mir-16; mir-291a-5p; |  |
|  | mir-291a-5p; mir-742; mir-153; |  | mir-23b |  |
|  | mir-106b; mir-130a; mir-130b; |  |  |  |
|  | mir-721; mir-93; |  |  |  |
|  | mir-25; mir-92b; |  |  |  |
|  | mir-19a; mir-361; |  |  |  |
|  | mir-351; mir-381 |  |  |  |
|  | mir-466d-5p; mir-760; mir-19a |  |  |  |
|  | mir-335-5p; mir-23b; mir-16; mir-106b; mir-93; |  |  |  |
|  | mir-18a; mir-295; mir-302b |  |  |  |
| 24 | mir-141 | BMP1 | mir-384-p | Runx2 |
|  |  |  | mir-384p | Dlx3 |
|  |  |  | mir-486 | Smad5 |

Runx2 - Runt domain transcription factor;
Msx2 - muscle segment 2 homeobox gene.
See Table 1 for description of the other genes and transcription factors.

In conclusion, a thorough evaluation of the effects due to various nanomaterials on cell calcification and bone matrix formation in MC3T3-E1 bone cells is very important, given the newly found nanoparticles-cells interactions and the nanoparticles-induced enhanced extracellular bone matrix formation. In this study, it was found that several nanomaterials induced calcification of MC3T3-E1 cells with the highest response being induced by the AgNPs. The enhanced magnitude of the mineralization and ALP expression in the cells incubated with AgNPs was significantly greater than the levels of the enzyme analyzed in the cells treated with the other nanomaterials studied (SWCNTs, $TiO_2$, and HA). Alizarin red staining is still the standard method to visualize mineralization in osteogenic cell cultures. In the present study the number of the nodules formed in the culture of bone cells treated with AgNPs was higher than those induced by the other nanomaterials and untreated control cells. In addition to these phenotypic responses, we found that the exposure of cells to AgNPs affected genes responsible for osteogenic differentiation. The miRNA analysis indicated that miRNA regulation and expression of essential transcriptional factors and bone morphogenetic proteins played an important role in activating the process of mineralization in bone cells exposed to AgNPs. To our knowledge, this is the first report that describes the regulation of a specific developmental activity by a nanomaterial resulting in a beneficial outcome.

Nanostructural Materials Preparation

Single wall carbon nanotubes utilized in this work were synthesized on the bi-metallic catalyst system Fe—Co supported on MgO [41]. The Fe:Co:MgO catalytic system with a stoichiometric composition of 2.5:2.5:95 wt.%, was prepared by the impregnation method as previously shown in our manuscripts [41, 42]. Single wall carbon nanotubes with small and uniform diameters were grown by Radio Frequency (RF) catalytic Vapor Deposition (cCVD), utilizing methane as a hydrocarbon source. About 100 mg of the catalyst was uniformly spread into a thin layer onto a graphite susceptor and placed in the center of a quartz tube. First, the tube was purged with the carrier gas (Argon) for 10 minutes at 150 ml/min. Next, the RF generator was turned on and when the temperature of the graphite boat reached 800° C., methane ($CH_4$) was introduced at 40 ml/min for 30 minutes [41]. At the end of the reaction, the system cooled down under the presence of Argon for 10 minutes. The as-produced SWCNTs were purified in one easy step using diluted hydrochloric acid solution and sonication. Their final purification determined by Thermo-Gravimetrical Analysis was found to be above 98%. SW-CNTs were added to the growth medium prior to cell culturing and the resultant fluid was sonicated to distribute the particles uniformly. The concentration of nanoparticles was determined by UV-Vis-NIR spectroscopy.

Figure 7:
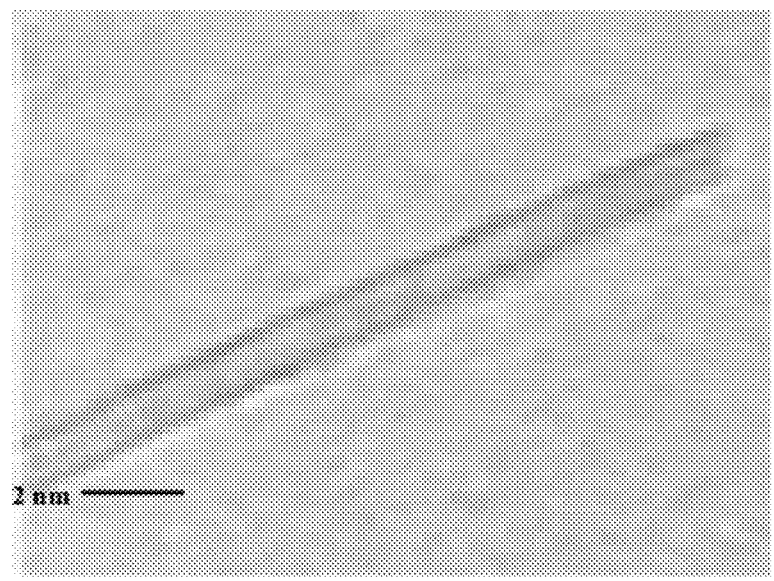
FIG. 7 is a TEM image of SWCNTs described herein wherein the SWCNTs have diameters of between 0.8-1.7 nm and are several microns in length.

TEM analyses were performed in order to characterize the morphological properties of SWCNTs. FIG. 7 shows the TEM image of the SWCNTs utilized in this work. The diameters of the SWCNTs vary between 0.8-1.7 nm and they are several microns in length [41].

Raman spectroscopy was also utilized to determine the diameter and the crystallinity of the SWCNTs. The vibrational modes observed Raman spectra of SWCNTs are the radial breathing mode (RBM), the D band, G band and the 2D band [43]. The RBM peaks are usually observed between 100 to 500 $cm^{-1}$ and their positions are strongly dependent on the diameter of the SWCNTs [44]. The D band, which is usually associated with the presence of defects in the CNT structure, it appears between 1305 and 1350 $cm^{-1}$. The G band or the tangential band is present between 1500 and 1605 $cm^{-1}$ and it corresponds to the stretching mode of the carbon-carbon bond in the graphene plane [45]. The 2D band or the second-order harmonic of the D band is usually present between 2500 and 2700 $cm^{-1}$ and is often associated with the degree of nanotube crystallinity [44].

Figure 8:
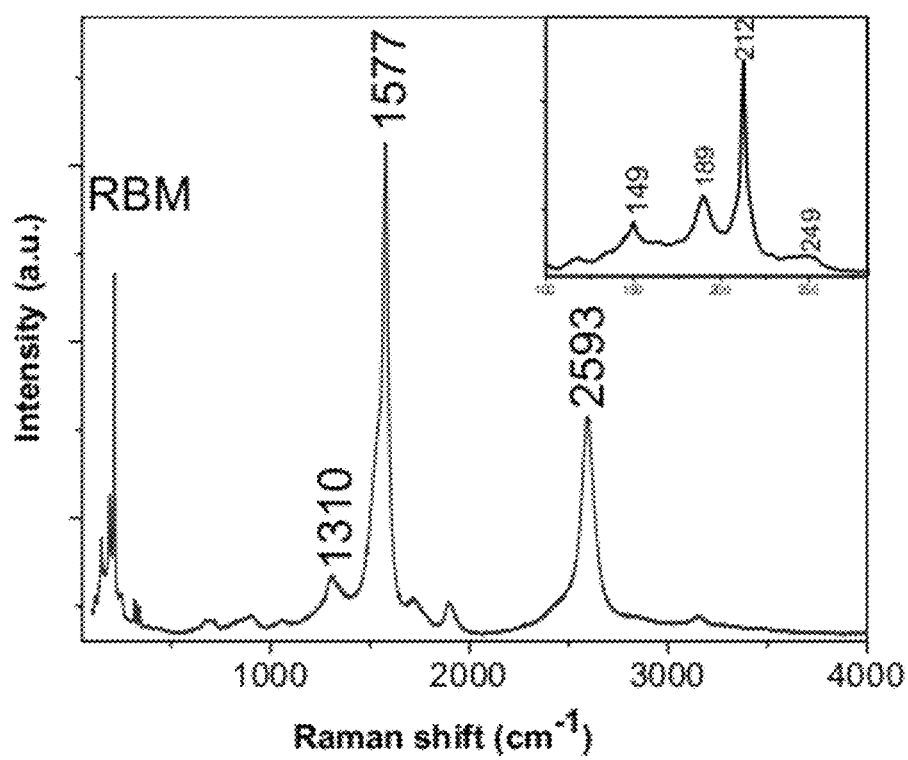
FIG. 8 is a Raman spectrum of SWCNTs collected with 633 nm laser excitation of the full frequency domains showing all the corresponding vibrational modes wherein the inset represents a magnified area of the RBM region.

FIG. 8 is a Raman spectrum of SWCNTs collected with 633 nm laser excitation of the full frequency domains showing all the corresponding vibrational modes wherein the inset represents a magnified area of the RBM region. As shown in the inset of FIG. 8, these SWCNTs exhibit very few peaks in the RBM region (between 149-249 $cm^{-1}$), which correspond to the nanotube diameters in the range of 0.8-1.7 nm. These results are in good agreements with the TEM analysis.

Silver NPs (purity of 99.999 wt. %) with the average diameter of 23.0+2.0 nm and the peak width at half-height of 7.1±1.5 nm were prepared by borohydrate mediated reduction of silver nitrate and was based on the following protocol: in deionized (DI) water sodium borohydrate was introduced followed by sodium citrate followed by $AgNO_2$ (drop wise) under slow stirring. Polyvinyl pyrrolidone (PVP) was added to the solution and the mixture was stirred for 30 minutes. The resulting product was a golden yellowish in color. The TEM analysis of the nanoparticles is shown in FIG. 9.

Figure 9:
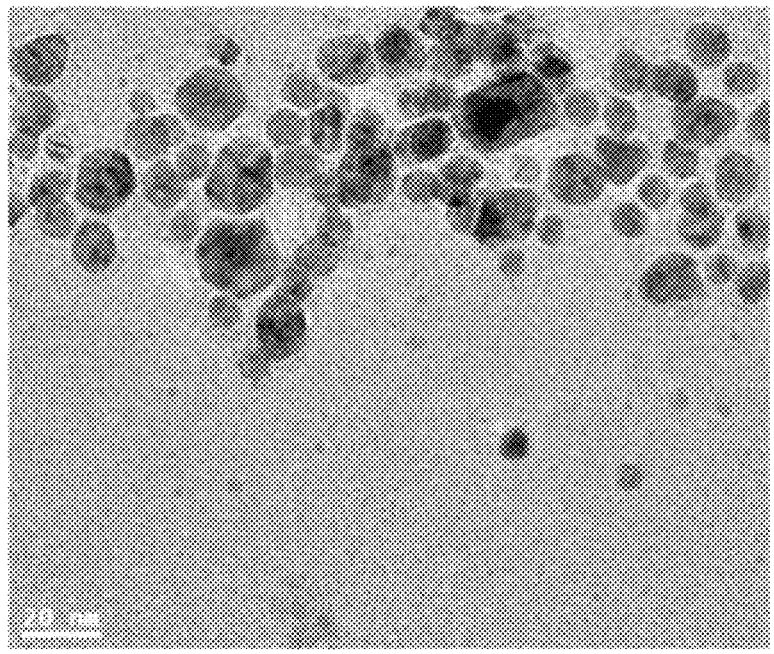
FIG. 9 is a TEM of the AgNPs described herein.

FIG. 9 is a TEM of the AgNPs used for this study.

Hydroxyapatite nanocrystals (HAP) were purchased from Berkeley Advanced Biomaterials Inc. and they had a diameter of 20±5 nm. The titanium dioxide nanoparticles ($TiO_2$) were purchased from Nanostructures and Amorphous Materials Inc. and had a diameter of 20±7 nm. The nanoparticles were all sonicated in the growth medium at a concentration of 20 µg/ml and were introduced to the cell culture and incubated for 24 hours.

Electron Microscopy Analysis

The specimens were analyzed by scanning electron microscopy (SEM) equipped with field emission source (JEOL JSM-7000F) and energy dispersive X-ray spectroscopy (EDS) (EDAX Genesis 2000).

Transmission electron microscopy (TEM) images were collected on a field emission JEM-2100F TEM (JEOL Inc.) equipped with a CCD camera. The acceleration voltage was 100 kV for the nanotube analysis. SWCNTs were homogeneously dispersed in 2-propanol under sonication for 30 min. Next, a few drops of the suspension were deposited on the TEM grid, dried, and evacuated before analysis.

Raman scattering spectra were recorded at room temperature using a Horiba Jobin Yvon LabRam HR800 equipped with a CCD camera. A spectrometer with a grating of 600 lines/mm and a He—Ne laser (633 nm) was used as excitation source. The laser beam intensity measured at the sample was kept at 5 mW, and Raman shifts were calibrated with a silicon wafer at a peak of 521 $cm^{-1}$.

Cell Culture

MC3T3 cells were purchased from ATCC Inc. and maintained according to instructions provided. They were plated in 100 mm culture dishes at a density of $10^6$/dish and supplemented by α-Minimum Essential Medium with 10% FBS and 1% PS and incubated in 37° C., 5% $CO_2$ humidified incubator. Once at confluence, the cells were EDTA trypsinized for further experiments. For experimental purposes, the cells were plated at a desired density in 24 well plates; $10^5$/well and incubated for 24 hours with 1 ml α-Minimum Essential Medium with 10% FBS and 1% PS with or without nanoparticles (20 µg/ml) of Ag-NPs, Hydroxyapatite, $TiO_2$ and SWCNTs; incubated in 37° C. in a 5% $CO_2$ humidified incubator for 6 days until cells are confluent and the medium was changed every 48-72 hrs by aspirating half the volume and add 0.5 ml of fresh medium for each well. The cells were supplemented with the differentiation media as described in the following sections.

Characterization of Bone Cells

Cells from the same passages were grown on 10 mm plastic cover slips at a density of ($1 \times 10^4$ cells/dish) for the SEM images and supplemented with the growth medium as previously described. For the microscopic visualization, the cells were grown on 60 mm dishes under the same conditions and stained by (TRACP & ALP double-stain Kit) according to the manufacturer procedure.

Osteogenesis Induction

The medium was aspirated and replaced by 1 ml of Osteogenesis Induction Medium #1, containing approximately 99% cell culture medium, 0.02 mM/ml Ascorbic Acid 2—Phosphate solution and 1 mM/ml Glycerol 2—Phosphate solution, this medium change corresponds to differentiation day 0 and was changed with 1 ml fresh Osteogenesis Induction Medium #1 every 2-3 days.

On differentiation day 9, the medium was replaced by 1 ml fresh Osteogenesis Induction Medium #2 by adding 5 nM/ml Melatonin solution to the Osteogenesis Induction Medium #1, the medium was replaced by fresh Osteogenesis Induction medium #2 every 2-3 days.

Osteogenesis Quantification Assay

After 24 days the cells were fixed by 10% formaldehyde for 10 minutes and washed 3 times for 5-10 minutes each with 1× Phosphate Buffer Saline and stained with an Alizarin Red Stain solution by adding 400 µl to each well and incubated for 30 minutes. The stain was drained and the cells were washed 3 times with 1× PBS for 5-10 minutes. For the osteogenesis quantification 400 µl 10% acetic acid was added to each well and incubated for 30 min with shaking to loosen the attached monolayer with the aid of a cell scraper; the cells and acetic acids were transferred to 1.5 ml micro-centrifuge tubes and vortexed vigorously for 30 seconds. The samples were heated to 85° C. for 10 minutes and transferred directly to ice for 5 minutes for cooling. The samples were centrifuged at 20,000 g for 15 minutes. Four hundred µl of the supernatant was removed to 1.5 ml microcetrifuge tubes and 150 µl of ammonium hydroxide solution was added to each tube to neutralize the pH and insure it falls within the range of 4.1-4.5. Four hundred µl of the standard/sample were removed to the spectrophotometer cuvette and read at $OD_{405}$ and the Alizarin Red stain concentration in each sample was plotted vs. $OD_{405}$. The Alizarin Red concentration in each sample was calculated according to the OD of the standard solution and the spectrophotometer was calibrated with a blank solution using 400 µl of 1× ARS dilution buffer.

Cells Viability Analysis and Trypan Blue Assay

The cytotoxic effects of the nanomaterials were determined by Trypan Blue exclusion, a well known standard method to detect cell viability. The cells were cultured for 24 hours with different nanomaterials at the concentrations of 20 µg/ml in the appropriate growth medium in a 48-well plate in a desired density. Then, the cells were dissociated with trypsin and transferred to 1.5 eppendorf tubes and centrifuged. Finally, 25 µL of 1× Trypan Blue dye was added to each sample and incubated for less than 5 min. The viable cell number was counted using a hemacytometer, and the viability values were compared to the negative control.

Alizarin Red Staining

Cells were washed once with distilled water and then fixed with phosphate-buffered formalin for 20 min. The fixed cells were also washed once with distilled water and subsequently stained with 1% alizarin red S solution for 5 min, the remaining dye was washed out twice with distilled water, and the cells were washed once more and then dehydrated with ethanol.

ALP Double Staining

After washing with PBS, the cells were incubated with Ag-NPs as described above for 3 different time points (6, 15, 24 days) and were fixed with the fixative solution (Citrate buffer (pH 5.4) containing 60% acetone and 10% methanol) for 10 min at room temperature. After fixation, the cells were washed thoroughly with PBS and incubated with the substrate solution for acid phosphatase for 30 min at 37° C., for double staining of the ALP; the cells were incubated with the substrate solution for the ALP after washing and incubated for another 30 min. For the nuclear staining the cells were stained with methyl green and incubated for 5 min at room temperature and washed 3 times with sterilized distilled water. The cells were visualized under the microscope.

Alkaline Phosphatase (ALPase) Activity Assay:

The bone cells were incubated with Ag-NPs as described above. Whole-cell extracts were collected at 0 day from the untreated cells and after 6 days of differentiation for the silver nanoparticles treated cells, and incubated for 60 min with 50 mM Tris-HCl (pH 8.8), 10 mM $MgCl_2$, and 20 mM of p-nitrophenylphosphate (p-NPP), at 37° C. Following incubation the absorbance at 405 nm was measured spectrphotometrically to quantify the amount of p-nitrophenylphosphate produced. Total cell protein was assayed according to the method described by the commercial kit supplier (TAKARA, ALPase assay).

miRNA Isolation

The cells were rinsed twice with cold 1× PBS and lysed in 600 µl RNA lysis/binding buffer (Ambion Inc., Austin, Tex.). miRNAs were isolated using mirVana™ miRNA isolation kit (Ambion) that specifically capture small RNAs with lengths of less than 200 nucleotides. The RNAs were initially eluted in 100 µl nuclease-free water (Ambion) and then dried using a DNA 110 SpeedVac vacuum concentrator (Savant) to increase RNA concentrations. RNA concentrations were determined using a NanoDrop 1000 Spectrophotometer (NanoDrop Technologies, Wilmington, Del.).

PCR Array Analysis of miRNA Expression

Two hundred nanograms of enriched small RNAs were converted into cDNA using $RT^2$ miRNA First Strand Kit (SABiosciences Corporation, Frederick, Md.). The cDNAs were mixed with 2× $RT^2$ SYBR Green PCR Master Mix (SABiosciences) and dispersed into 384-well Mouse Genome miRNA PCR Array (MAM-3100E, SABiosciences) with 10 µl/well reaction mix. The PCR array contained a panel of primer sets for 376 mouse miRNAs, four small RNAs as the internal controls and four quality controls. The real-time qRT-PCR was performed on a 7900 real-time PCR system (Applied Biosystems Inc., Foster City, Calif.) with the following cycling parameters: 95° C. for 10 min, then 40 cycles of 95° C. for 15 s, 60° C. for 30 s and 72° C. for 30 s. SYBR Green fluorescence was recorded from every well during the annealing step of each cycle. The threshold cycle (Ct) value of each sample was calculated with software SDS 2.3 (Applied Biosystems). To calculate Cts, we set the threshold line as 0.15 and kept it the same across all of the analyses. The baseline was automatically defined by the software.

Normalization and Statistical Analysis

Normalization and statistical analysis of miRNA expression were conducted using SABiosciences' Online PCR Array Data Analysis Web Portal. The ΔΔCt method was utilized to calculate the fold change (FC). Four genes, snoRNA251, snoRNA202, snoRNA142, and U6 in the PCR arrays, were used as endogenous controls to normalize each sample. To determine the effects of nanoparticle treatment, the formula: $FC=2^{\wedge}$ [−(mean of ΔCt values of nanoparticle-treated samples at a specified time point−mean of ΔCt values of control samples at the same time point)] was used for up-regulated genes, while $FC=-2^{\wedge}$ (mean of ΔCt values of nanoparticle-treated samples at a specified time point−mean of ΔCt values of control samples at the same time point) was used for the down-regulation genes, and p values were calculated using t-tests between nanoparticle-treated and control samples at each time point to determine whether there was a significant difference for miRNA expression. To determine the miRNA response in untreated MC3T3 cell, the formula: $FC=2^{\wedge}$ [−(mean of ΔCt values of samples after initiation of the MC3T3 cell culture−mean of ΔCt values of control samples at day 0)] was used for up-regulated genes, while $FC=-2^{\wedge}$ (mean of ΔCt values of samples after initiation of MC3T3 cell culture−mean of ΔCt values of control samples at day 0) was used for the down-regulations, and p values were calculated using t-tests between day 0 samples and samples at each of the subsequent time points to determine whether there is a significant difference for miRNA expression.

Prediction of Target Genes

The predicted target genes of differentially expressed microRNAs were obtained from TargetScan database (http://www.targetscan.org/). TargetScan predicts biological targets of microRNAs by searching for the presence of conserved 8 mer and 7 mer sites that match the seed region of each miRNA [46, 47]. TargetScan is a widely used database for microRNA target gene prediction and was demonstrated that its prediction matches best with the experimental data from proteomics [48].

While the foregoing specification teaches the principles of the present invention, with examples provided for the purpose of illustration, it will be appreciated by one skilled in the art from reading this disclosure that various changes in form and detail can be made without departing from the true scope of the invention.

REFERENCES

[1] Usui, Y.; Aoki, K.; Narita, N.; Murakami, N.; Nakamura, I.; Nakamura, K.; Ishigaki, N.; Yamazaki, H.; Horiuchi, H.; Kato, H.; Taruta, S.; Kim, Y.-A.; Endo, M.; Saito, N. Carbon Nanotubes with High Bone-Tissue Compatibility and Bone-Formation Acceleration Effects. *Small,* 2008, 4, 240-246.

[2] Oh, S.; Daraio, C.; Chen, L.-H.; Pisanic, T.; Finones, R.; Jin, S. Significantly Accelerated Osteoblast Cell Growth On Aligned $TiO_2$ Nanotubes. *J. Biomed. Mat. Res. Part A,* 2005, DOI 10.1002/jbm.a, 97-103.

[3] Wen, H.-C.; Lin, Y.-N.; Jian, S.-R.; Tseng, S.-C.; Weng, M.-X.; Liu, Y.-P.; Lee, P.-T.; Chen, P.-Y.; Hsu, R.-Q.; Wu, W.-F.; Chou, C.-P. Observation of Growth of Human Fibroblasts on Silver. *J. Phys.: Conf Ser.* 2007, 61, 445-449

[4] Zhang, L.; Webster, T. J. Nanotechnology and nanomaterials: Promises for improved tissue regeneration. *Nanotoday,* 2009, 4, 66-80.

[5] Dobson, J. Gene therapy progress and prospects: Magnetic nanoparticle-based gene delivery, *Gene Therapy,* 2006, 13, 283-287, doi:10.1038/sj.gt.3302720.

[6] Zhang, J. C.; Li, X, X.; Xu, S. J.; Wang, K.; Yu, S. F.; Lin, Q. Effects of rare earth ions on proliferation, differentiation and function expression of cultured osteoblasts in vitro. *Prog. Nat. Sci.,* 2004, 14, 404-409.

[7] Dean, D. D.; Schwartz, Z.; Bonewald, L.; Muniz, O. E.; Morales, S.; Gomez, R.; Brooks B. P.; Qiao, M.; Howell, D. S.; Boyan, B. D. Matrix vesicles produced by osteoblast-like cells in culture become significantly enriched in proteoglycan-degrading metalloproteinases after addition of beta-glycerophosphate and ascorbic acid. *Calc Tissue Int.* 1994, 54, 399-408.

[8] Matsumoto, T.; Igarashi, C.; Takeuchi, Y.; Harada, S.; Kikuchi, T.; Yamato, H.; Ogata, E. Stimulation by 1,25-dihydroxyvitamin D3 of in vitro mineralization induced by osteoblast-like MC3T3-E1 cells. *Bone* 1991, 12, 27-32.

[9] Mahmood, M.; Casciano, D. A.; Mocan, T.; Iancu, C.; Xu, Y.; Mocan, L.; Todea-Iancu, D.; Dervishi, E.; Li, Z.; Abdalmuhsen, M.; Biris, A. R.; Ali, N.; Biris, A. Cytotoxicity and Biological Effects of Functional Nanomaterials Delivered to Various Cell Lines. *J. App. Tox.* 2010, 30, 74-83.

[10] Wen, H.-C.; Lin, Y.-N.; Jian, S.-R.; Tseng, S.-C; Weng, M.-X.; Liu, Y.-P.; Lee, P.-T.; Chen, P.-Y.; Hsu, R.-Q.; Wu, W-F.; Chou, C.-P. Observation of Growth of Human Fibroblasts on Silver Nanoparticles. *J. of Phys.* 2007, 61, 445-449.

[11] Doering, W. E.; Nie, S. Single-Molecule and Single-Nanoparticle SERS: Examining the Roles of Surface Active Sites and Chemical Enhancement. *J. of Phys. Chem. B.,* 2002 106, 311-317.

[12] Botelho, C. M.; Brooks, R. A.; Best, S. M.; Lopes, M. A.; Santos, J. D.; Rushton, N.; Bonfield, W. Human osteoblast response to silicon-substituted hydroxyapatite. *J Biomed Mater Res A.* 2006, 79, 723-30.

[13] Chang, Y. L.; Stanford, C. M.; Keller, J. C. Calcium and phosphate supplementation promotes bone cell mineralization: Implications for hydroxyapatite (HA)-enhanced bone formation. *J. of Biomed. Mat. Res.* 2000, 52, 270-278.

[14] Liao, H.; Wurtz, T.; Li, J. Influence of titanium ion on mineral formation and properties of osteoid nodules in rat calvaria cultures. *J. Biomed. Mater. Res.* 1999, 47, 220-227.

[15] Liao, H.; Wurtz, T.; Li, J. Influence of titanium ion on mineral formation and properties of osteoid nodules in rat calvaria cultures. *J. Biomed. Mat. Res.* 1999, 47, 220-227.

[16] Chen, R. J.; Bangsaruntip, S.; Drouvalakis, K. A.; Wong Shi Kam, N.; Shim, M.; Li, Y.; Kim, W.; Utz, P. J.; Dai, H. Noncovalent functionalization of carbon nanotubes for highly specific electronic biosensors. *PNAS,* 2003, 100, 4984-4989.

[17] Shi, X.; Sitharaman, B.; Pham, Q. P.; Spicer, P. P.; Hudson, J. L.; Wilson, L. J.; Tour, J. M.; Raphael, R. M.; Mikos, A. G. In vitro cytotoxicity of single-walled carbon nanotube/biodegradable polymer nanocomposites. *J. of Biomed. Mat. Res.* 2007, 86A, 813-823.

[18] Zhang, D.; Yi, C.; Zhang, J.; Chen, Y.; Yao, X.; Yang, M. The effects of carbon nanotubes on the proliferation and differentiation of primary osteoblasts. *Nanotechnology,* 2007, 18, 475102.

[19] Magrez, A.; Kasas, S.; Salicio, V.; Pasquier, N.; Seo, J.-W.; Celio, M.; Catsicas, S.; Schwaller, B.; Forr, L. Cellular Toxicity of Carbon-Based Nanomaterials, *Nano Lett.,* 2006, 6, 1121-1125.

[20] Mahmood, M., Karmakar, A.; Fejleh, A.; Mocan, T.; Iancu, C.; Mocan, L.; Todea Iancu, Y D.; Xu, Y.; Dervishi, E.; Li, Z.; Biris, A. R.; Agarwal, R.; Ali, N.; Galanzha, E. I.; Biris, A. S.; Zharov, V. P.; Synergistic enhancement of cancer therapy using a combination of carbon nanotubes and anti-tumor drug. *Nanomedicine,* 2009, 4, 883-893, DOI 10.2217/nnm.09.76

[21] Dervishi, E.; Li, Z.; Watanabe, F.; Xu, Y.; Saini, V.; Biris, A. R.; Biris, A. S. Thermally controlled synthesis of single-wall carbon nanotubes with selective diameters. *J. Mater. Chem.,* 2009, 19, 3004-3012

[22] Dervishi, E.; Li, Z.; F.; Xu, Y.; Saini, V.;. Watanabe, F.; Biris, A. R.; Bonpain, A.; Garbay, J. J; Meriet, A.; Richard, M.; Biris, A. S. The Influence of Fe—Co/MgO Catalyst Composition on the Growth Properties of Carbon Nanotubes. *Part. Sci. and Tech.,* 2009, 27, 222-237.

[23] Montjovent, M-O.; Burri, N.; Silke, M.; Federici, E.; Scalett, C.; Zambelli, P-Y.; Hohlfeld, P.; Leyvraz, P-F.; Applegate, L. L.; Pioletti, D. P.; Fetal bone cells for tissue engineering. *Bone,* 2004, 35; 1323-13331.

[24] Kawazoe, Y.; Shiba, T.; Nakamura, R.; Mizuno, A.; Tsutsumi, K.; Uematsu, T.; Yamaoka, M.; Shindoh, M. and Kohgo, T. Induction of Calcification in MC3T3-E1 Cells by Inorganic Polyphosphate, *J. Dent Res,* 2004, 83(8):613-6182.

[25] Bellows, C. G.; Aubin, J. E.; Heersche, J. N.; Antosz, M. E. Mineralized bone nodules formed in vitro from enzymatically released rat calvaria cell populations. *Calcif. Tissue Int,* 1986, 38, 143-154.

[26] Gerstenfeld, L, C.; Chipman, S. D.; Glowacki, J.; Lian, J. B, Expression of differentiated function by mineralizing cultures of chicken osteoblasts. *Dev Biol,* 1987, 122, 49-60.

[27] Bellows, C. G.; Aubin, J. E.; Heersche, J. N. Physiological concentrations of glucocorticoids stimulate formation

[28] Marsh, M. E.; Munne, A. M.; Vogel, J. J.; Cui, Y.; Franceschi, R. T.; Mineralization of bone-like extracellular matrix in the absence of functional osteoblasts. *J Bone Miner Res*, 1995, 10, 1635-1643.

[29] Owen, T. A.; Aronow, M.; Shalhoub, V.; Barone, L. M.; Wilming, M. S.; Tassinari M. S.; Kennedy, M. B.; Pockwinse, S.; Lian, J. B.; Stein, G. S. Progressive development of the rat osteoblast phenotype in vitro: reciprocal relationships in expression of genes associated with osteoblast proliferation and differentiation during formation of the bone extracellular matrix. *J. Cell Physiol*, 1990, 143, 420-430.

[30] Chen, D.; Chen, H.; Feng, J. Q.; Windle, J. J.; Koop, B. A.; Harris, L. F.; Bonewald, L. F.; Boyce, B. F.; Wozney, J. M.; Mundy, G. R.; Harris, S. E. Osteoblastic cell lines derived from a transgenic mouse containing the osteocalcin promoter driving SV40 T-antigen. *Mol. Cell Diff.*, 1995, 3, 193-212.

[31] Gregory, C. A.; Grady Gunn, W.; Peister, A.; Prockop, D. W. An Alizarin red-based assay of mineralization by adherent cells in culture: comparison with cetylpyridinium chloride extraction. *Anal. Biochem.* 2004, 329, 77-84.

[32] Breen, E. C.; Ignotz, R. A.; McCabe, L.; Stein, J. L.; Stein, G. S.; Lian, J. B. TGF beta alters growth and differentiation related gene expression in proliferating osteoblasts in vitro, preventing development of the mature bone phenotype. *J. Cell Physiol.* 1994, 160, 323-335.

[33] Katayama, U. K.; Miyamoto, T.; Koshihara, T.; Interleukin-4 enhances in vitro mineralization in human osteoblast-like cells. *Biochem Biophys Res Commun*, 1992, 189, 1521-1526.

[34] Rey, C.; Kim, H. M.; Gerstenfeld, L.; Glimcher, M. J.; Structural and chemical characteristics and maturation of the calcium phosphate crystals formed during the calcification of the organic matrix synthesized by chicken osteoblasts in cell culture. *J Bone Miner Res*, 1995, 10, 1577-1588.

[35] Brodersen, P.; Voinnet, O. Revisiting the principles of microRNA target recognition and mode of action. *Nat. Rev. in Mol. and Cell Bio.* 2009, 10, 141-148.

[36] Chen T. The role of microRNA in chemical carcinogenesis. *J. of Env. Sci. and Health, Part C*, 2010, 28, 1-36.

[37] Li, Z.; Hassan, M. Q.; Volinia, S.; van Wijnen, A. J.; Stein, J. L.; Croce, C. M.; Lian, J. B.; Stein, G. S. A microRna signature for a BMP-induced osteoblast lineage commitment program. *Proc. Natl. Acd. Sci., USA*, 2008, 105, 13906-13911.

[38] Chen, D.; Zhao, M.; Mundy, G. R. Bone morphogenetic proteins. *Growth Factors*, 2004, 22, 233-241.

[39] Beck, G. R. Jr; Sullivan, E. C.; Moran, E.; Zerler, B. Relationship between alkaline phosphatase levels, osteopontin expression, and mineralization in differentiating MC3T3-E1 osteoblasts. *J. Cell Biochem.* 1998, 68, 269-280.

[40] Lee, K. S.; Kim, H. J.; Li, Q-L.; Chi, X-Z.; Ueta, C.; Komori, T.; Wozney, J. M.; Kim, E. G. Choi, J-Y.; Ryoo, H-M.; Bae, S. C. Runx2 Is a Common Target of Transforming Growth Factor beta 1 and Bone Morphogenetic Protein 2, and Cooperation between Runx2 and Smad5 Induces Osteoblast-Specific Gene Expression in the Pluripotent Mesenchymal Precursor Cell Line C2C12. *Mol. and Cell. Bio.*, 2000, 20, 8783-8792.

[41] Dervishi, E.; Li, Z.; Watanabe, F.; Xu, X.; Saini, V.; Biris, A. R.; Biris, A. S. Thermally controlled synthesis of single-wall carbon nanotubes with selective diameters. *J. Mater. Chem.*, 2009, 19, 3004-3012.

[42] Dervishi, E.; Li, Z.; F.; Xu, Y.; Saini, V.; Watanabe, F.; Biris, A. R.; Bonpain, A.; Garbay, J. J; Meriet, A.; Richard, M.; Biris, A. S. The Influence of Fe—Co/MgO Catalyst Composition on the Growth Properties of Carbon Nanotubes. *Part. Sci. and Tech.*, 2009, 27, 222-237.

[43] Rao, A. M.; Chen, J.; Richter, E.; Schlecht, E.; Eklund, P. C.; Haddon, R. C.; Venkateswaran, U. D.; Kwon, Y.-K.; Tomanek, D. *Phys. Rev. Lett.*, 2001, 86, 3895-3898.

[44] Dresselhaus, M. S.; Dresselhaus, G.; Jorio, A.; Souza Filho, A. G.; Saito, R. *Carbon*, 2002, 40, 2043-2061.

[45] Strong, K. L.; Anderson, D. P.; Lafdi, K.; Kuhn, J. N. Purification process for single-wall carbon nanotubes. *Carbon*, 2003, 41, 1477-1488.

[46] Lewis, B. P.; Burge, C. B; Bartel, D. P. Conserved seed pairing, often flanked by adenosines, indicates that thousands of human genes are microRNA targets. *Cell*, 2005, 120, 15-20.

[47] Grimson, A.; Farh, K. K.; Johnston, W. K.; Garrett-Engele, P.; Lim, L. P.; Bartel, D. P. MicroRNA targeting specificity in mammals: determinants beyond seed pairing. *Mol. Cell*, 2007, 27, 91-105.

[48] Baek, D.; Villén, J.; Shin, C.; Camargo, F. D.; Gygi, S. P.; Bartel, D. P. The impact of microRNAs on protein output. *Nature*, 2008, 455, 64-71.

What is claimed is:

1. A method comprising:
   contacting a bone cell with loose nanoparticles;
   wherein the loose nanoparticles are internalized into the bone cell and induce mineralization in the bone cell
   wherein the loose nanoparticles are selected from the group consisting of silver nanoparticles, $TiO_2$ nanoparticles, hydroxyapatite nanoparticles, single-walled carbon nanotubes and combinations thereof.

2. The method of claim 1, wherein the loose nanoparticles comprise $TiO_2$ nanoparticles.

3. The method of claim 1, wherein the loose nanoparticles comprise hydroxyapatite nanoparticles.

4. The method of claim 1, wherein the loose nanoparticles are coated with a layer of polymer.

5. The method of claim 1, wherein the loose nanoparticles are attached to one or more targeting moieties.

6. The method of claim 5, wherein the targeting moieties are selected from the group consisting of antibodies, folates, growth factors, and combinations thereof.

7. The method of claim 1, wherein the loose nanoparticles are spherical nanoparticles, nanorods, nanotubes or flat sheets.

8. The method of claim 1, wherein the loose nanoparticles are in a composition which further comprises a pharmaceutically acceptable carrier.

9. The method of claim 1, wherein the loose nanoparticles comprise silver nanoparticles.

10. The method of claim 9, wherein the silver nanoparticles have an average diameter of 20±4 nm.

11. The method of claim 1, wherein the loose nanoparticles comprise single-walled carbon nanotubes.

12. The method of claim 11, wherein the single-walled carbon nanotubes have a diameter of 0.8 to 1.7 nm.

13. The method of claim 1, wherein the bone cell is an osteoblast cell.

14. A method for increasing bone mass, bone healing or bone formation comprising administering to a subject in need thereof an effective amount of a composition comprising loose nanoparticles;

wherein the loose nanoparticles are internalized into the bone cell and induce mineralization in the bone cell wherein the loose nanoparticles are selected from the group consisting of silver nanoparticles, $TiO_2$ nanoparticles, hydroxyapatite nanoparticles, single-walled carbon nanotubes and combinations thereof.

15. The method of claim 14, wherein the loose nanoparticles comprise $TiO_2$ nanoparticles.

16. The method of claim 14, wherein the loose nanoparticles comprise hydroxyapatite nanoparticles.

17. The method of claim 14, wherein the loose nanoparticles comprise single-walled carbon nanotubes.

18. The method of claim 14, wherein the loose nanoparticles are coated with a layer of polymer.

19. The method of claim 14, wherein the loose nanoparticles are attached to one or more targeting moieties.

20. The method of claim 19, wherein the targeting moieties are selected from the group consisting of antibodies, folates, growth factors, and combinations thereof.

21. The method of claim 14, wherein the loose nanoparticles are spherical nanoparticles, nanorods, nanotubes or flat sheets.

22. The method of claim 14, wherein the loose nanoparticles are in a composition which further comprises a pharmaceutically acceptable carrier.

23. The method of claim 14, wherein the loose nanoparticles comprise silver nanoparticles.

24. The method of claim 23, wherein the silver nanoparticles have an average diameter of 20±4 nm.

25. The method of claim 14, wherein the subject suffers from a bone disease.

26. The method of claim 25, wherein the bone disease is osteoporosis.

27. The method of claim 14, wherein the subject suffers from a bone fracture.

28. The method of claim 27, wherein the method comprises contacting bone cells near the bone fracture site with the loose nanoparticles.

* * * * *